United States Patent
Constantinides (10) Patent No.: US 12,248,638 B2
(45) Date of Patent: Mar. 11, 2025

(54) POSE AND GESTURE DETECTION FOR CONTROL OF ULTRASOUND IMAGING SYSTEMS

(71) Applicant: Exo Imaging, Inc., Redwood City, CA (US)

(72) Inventor: Tony Constantinides, San Francisco, CA (US)

(73) Assignee: Exo Imaging, Inc., Santa Clara, CA (US)

(*) Notice: Subject to any disclaimer, the term of this patent is extended or adjusted under 35 U.S.C. 154(b) by 0 days.

(21) Appl. No.: 18/319,722

(22) Filed: May 18, 2023

(65) Prior Publication Data
US 2024/0385689 A1   Nov. 21, 2024

(51) Int. Cl.
| | | |
|---|---|---|
| *G06F 3/01* | (2006.01) | |
| *A61B 8/00* | (2006.01) | |
| *G06V 10/82* | (2022.01) | |
| *G06V 40/20* | (2022.01) | |

(52) U.S. Cl.
CPC ............. *G06F 3/017* (2013.01); *A61B 8/467* (2013.01); *A61B 8/54* (2013.01); *G06V 10/82* (2022.01); *G06V 40/28* (2022.01)

(58) Field of Classification Search
CPC ........ G06F 3/017; G06F 3/0346; G06F 3/011; G06F 2203/04108; G06F 2203/04802; G06F 3/04842; G06F 3/043; G06F 3/041–047; G06F 2203/041–04114; G06V 40/28; G06V 10/82; G06V 40/20; G06V 40/113; G06V 40/23; A61B 8/467; G06T 2207/20084
See application file for complete search history.

(56) References Cited

U.S. PATENT DOCUMENTS

| | | | |
|---|---|---|---|
| 10,955,932 B1 | 3/2021 | Saba et al. | |
| 2015/0172536 A1* | 6/2015 | Sabourin | G06F 3/017 |
| | | | 348/77 |
| 2017/0252002 A1 | 9/2017 | Mine et al. | |
| 2018/0344284 A1 | 12/2018 | Freudenberger et al. | |
| 2021/0117660 A1* | 4/2021 | Risco | G06V 40/28 |
| 2021/0191611 A1* | 6/2021 | Wang | G06F 3/017 |
| 2023/0244315 A1* | 8/2023 | Pechin | G06V 20/46 |

FOREIGN PATENT DOCUMENTS

| | | |
|---|---|---|
| CN | 114886459 A | 8/2022 |
| WO | 2020112377 A1 | 6/2020 |

OTHER PUBLICATIONS

"Pose Detection," ML Kit; Last updated Feb. 1, 2023 UTC; accessed May 23, 2023; retrieved at https://developers.google.com/ml-kit/vision/pose-detection; 2 pages.
PCT International Search Report and Written Opinion issued in PCT/US2023/022683, dated Feb. 15, 2024; 11 pages.

* cited by examiner

*Primary Examiner* — Sanjiv D. Patel
(74) *Attorney, Agent, or Firm* — Alliance IP, LLC (57) ABSTRACT

An ultrasound imaging system is controlled by pose and/or gesture detection. The system may detect poses or gestures performed by a user, e.g., using a machine learning (ML) model that may include a neural network, and implement a command associated with the detected pose or gesture to control the ultrasound imaging system.

20 Claims, 8 Drawing Sheets

POSE AND GESTURE DETECTION FOR CONTROL OF ULTRASOUND IMAGING SYSTEMS

FIELD

Embodiments relate in general to the field of ultrasonic imaging devices and systems.

BACKGROUND

Ultrasound imaging is widely used in the field of medical imaging, for example, to image internal tissue, bones, blood flow, or organs of human or animal bodies in a non-invasive manner. To perform ultrasound imaging, an ultrasound imaging device may transmit an ultrasonic signal into the body and receive a reflected signal from the body part being imaged. Ultrasound imaging devices and/or systems are typically controlled through touch-based interactions with the device/system, e.g., by pressing buttons of the device or touching/tapping icons on a touch-based display.

SUMMARY

Disclosed embodiments may operate according to one or more sets of instructions, using algorithms, either collectively or individually, to detect poses and/or gestures of a user and control an ultrasound imaging system based on the detected poses or gestures.

BRIEF DESCRIPTION OF THE DRAWINGS

Some of the features of the embodiments are set forth with particularity in the appended claims. A better understanding of the features and advantages of embodiments will be obtained by reference to the following detailed description, in which the principles of the embodiments are utilized, and the accompanying drawings (also "Figure" and "FIG." herein), of which:

DETAILED DESCRIPTION

Embodiments herein provide techniques to control an ultrasound imaging system using pose and/or gesture detection. Pose and gesture detection can be performed using a machine learning (ML) model (e.g., one that includes a neural network (NN)) to estimate the pose of a person, or portion of the person, from an image or video based on determining spatial locations of particular body points (e.g., joints), which may be referred to as "keypoints". An ML model can be trained to monitor the position and/or changes in position of the keypoints to detect whether a particular pose or gesture has been performed by a user, and the detected pose or gesture can be used to control operation of one or more aspects of an ultrasound imaging system.

For instance, pose/gesture detection software may receive data from a camera of the ultrasound imaging system (e.g., a user-facing camera) and can analyze the received image/video data to determine whether a pose or gesture has been performed by a user, e.g., with their hand, arm, or other body part. The software can then cause a control command to be implemented in the ultrasound imaging system. For example, a user may perform a certain pose or gesture to cause the system to take a snapshot of an image currently being displayed, select an item/button on a display, etc.

In certain embodiments, the pose/gesture detection software can detect the pose or gesture and then pass an indication of the detected pose or gesture to control software of the ultrasound system, which can then interpret the pose or gesture as a particular command. However, in other embodiments, the pose/gesture detection software may also match the pose/gesture with a particular command, and then provide the corresponding command to the control software of the system.

Using pose and gesture detection to control an ultrasound imaging system can provide one or more advantages over traditional input methods for such systems. For example, pose/gesture detection can allow for control of the ultrasound imaging system in lieu of traditional inputs, such as a keyboard, buttons, touchscreen, etc., which can be beneficial in medical or other types of fields where there are sanitary concerns. In addition, it may also provide for control of the system in parallel with commands or inputs provided via traditional inputs, to provide for multiple input paths to the system at a time.

Additional aspects and advantages of some embodiments will become readily apparent to those skilled in this art from the above detailed description, wherein only illustrative embodiments are shown and described. As will be realized, some embodiments are capable of achieving other, different goals, and their several details are capable of modifications in various obvious respects, all without departing from the disclosure. Accordingly, the drawings and description are to be regarded as illustrative in nature, and not as restrictive.

In the following description, for purposes of explanation, specific details are set forth in order to provide an understanding of the disclosure. It will be apparent, however, to one skilled in the art that the disclosure may be practiced without these details. Furthermore, one skilled in the art will recognize that examples of the present disclosure, described below, may be implemented in a variety of ways, such as a process, one or more processors (processing circuitry) of a control circuitry, one or more processors (or processing circuitry) of a computing device, a system, a device, or a method on a tangible computer-readable medium.

One skilled in the art shall recognize: (1) that certain fabrication operations may optionally be performed; (2) that operations may not be limited to the specific order set forth herein; and (3) that certain operations may be performed in different orders, including being done contemporaneously, and (4) operations may involve using Artificial Intelligence.

Elements/components shown in diagrams are illustrative of exemplary embodiments and are meant to avoid obscuring the disclosure. Reference in the specification to "one example," "preferred example," "an example," "examples," "an embodiment," "some embodiments," or "embodiments" means that a particular feature, structure, characteristic, or function described in connection with the example is included in at least one example of the disclosure and may be in more than one example. The appearances of the phrases "in one example," "in an example," "in examples," "in an embodiment," "in some embodiments," or "in embodiments" in various places in the specification are not necessarily all referring to the same example or examples. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

Figure 1:
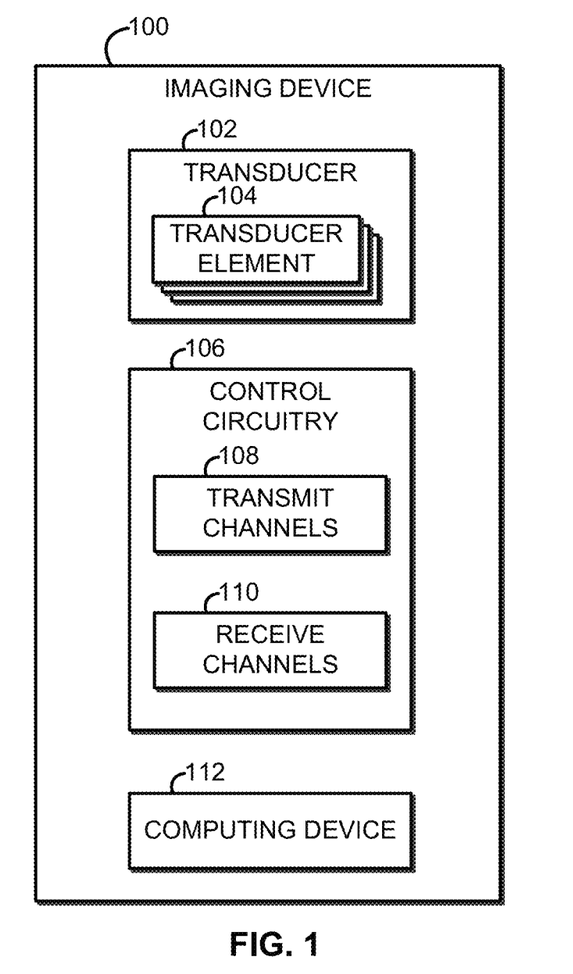
FIG. 1 is a block diagram of an imaging device in accordance with disclosed embodiments.

Turning now to the figures, FIG. 1 is a block diagram of an imaging device 100 in accordance with disclosed embodiments. The imaging device 100 includes a controller or control circuitry 106 that controls activation of the channels 108, 110, and further includes a computing device 112 to process signals sent to, or received from, the channels 108, 110. As described above, the ultrasound imaging device 100 may be used to generate an image of internal tissue, bones, blood flow, or organs of human or animal bodies. Accordingly, the ultrasound imaging device 100 may transmit a signal into the body and receive a reflected signal from the body part being imaged. Such imaging devices may include either piezoelectric micromachined ultrasound transducers (pMUTs) or capacitive micromachine ultrasonic transducers (cMUTs), which may be referred to as transducers or imagers, which may be based on photo-acoustic or ultrasonic effects. The ultrasound imaging device 100 may be used to image other objects as well. For example, the ultrasound imaging device may be used in medical imaging; flow measurements in pipes, speaker, and microphone arrays; lithotripsy; localized tissue heating for therapeutic; and highly intensive focused ultrasound (HIFU) surgery.

In addition to use with human patients, the ultrasound imaging device 100 may be used to acquire an image of internal organs of an animal as well. Moreover, in addition to imaging internal organs, the ultrasound imaging device 100 may also be used to determine direction and velocity of blood flow in arteries and veins as in Doppler mode imaging and may also be used to measure tissue stiffness.

The ultrasound imaging device 100 may be used to perform different types of imaging. For example, the ultrasound imaging device 100 may be used to perform one-dimensional imaging, also known as A-Scan, two-dimensional imaging, also known as B scan, three-dimensional imaging, also known as C scan, and Doppler imaging (that is, the use of Doppler ultrasound to determine movement, such as fluid flow within a vessel). The ultrasound imaging device 100 may be switched to different imaging modes, including without limitation linear mode and sector mode, and electronically configured under program control.

To facilitate such imaging, the ultrasound imaging device 100 includes one or more ultrasound transducers 102, each transducer 102 including an array of ultrasound transducer elements 104. Each ultrasound transducer element 104 may be embodied as any suitable transducer element, such as a pMUT or cMUT element. The transducer elements 104 operate to 1) generate the ultrasonic pressure waves that are to pass through the body or other mass and 2) receive reflected waves (received ultrasonic energy) off the object within the body, or other mass, to be imaged. In some examples, the ultrasound imaging device 100 may be configured to simultaneously transmit and receive ultrasonic waveforms or ultrasonic pressure waves (pressure waves in short). For example, control circuitry 106 may be configured to control certain transducer elements 104 to send pressure waves toward the target object being imaged while other transducer elements 104, at the same time, receive the pressure waves/ultrasonic energy reflected from the target object, and generate electrical charges based on the same in response to the received waves/received ultrasonic energy/received energy.

In some examples, each transducer element 104 may be configured to transmit or receive signals at a certain frequency and bandwidth associated with a center frequency, as well as, optionally, at additional center frequencies and bandwidths. Such multi-frequency transducer elements 104 may be referred to as multi-modal elements 104 and can expand the bandwidth of the ultrasound imaging device 100. The transducer element 104 may be able to emit or receive signals at any suitable center frequency, such as about 0.1 to about 100 megahertz. The transducer element 104 may be configured to emit or receive signals at one or more center frequencies in the range from about 0.1 to about 100 megahertz.

To generate the pressure waves, the ultrasound imaging device 100 may include a number of transmit (Tx) channels 108 and a number of receive (Rx) channels 110. The transmit channels 108 may include a number of components that drive the transducer 102, i.e., the array of transducer elements 104, with a voltage pulse at a frequency that they are responsive to. This causes an ultrasonic waveform to be emitted from the transducer elements 104 towards an object to be imaged.

According to some embodiments, an ultrasonic waveform may include one or more ultrasonic pressure waves transmitted from one or more corresponding transducer elements of the ultrasound imaging device substantially simultaneously. The ultrasonic waveform travels towards the object to be imaged and a portion of the waveform is reflected back to the transducer 102, which converts it to an electrical energy through a piezoelectric effect. The receive channels 110 collect electrical energy thus obtained, and process it, and send it for example to the computing device 112, which develops or generates an image that may be displayed.

In some examples, while the number of transmit channels 108 and receive channels 110 in the ultrasound imaging device 100 may remain constant, and the number of transducer elements 104 that they are coupled to may vary. A coupling of the transmit and receive channels to the transducer elements may be, in one embodiment, controlled by control circuitry 106. In some examples, for example as shown in FIG. 1, the control circuitry may include the transmit channels 108 and the receive channels 110. For example, the transducer elements 104 of a transducer 102 may be formed into a two-dimensional spatial array with N columns and M rows. In a specific example, the two-dimensional array of transducer elements 104 may have 128 columns and 32 rows. In this example, the ultrasound imaging device 100 may have up to 128 transmit channels 108 and up to 128 receive channels 110. In this example, each transmit channel 108 and receive channel 110 may be coupled to multiple or single pixels. For example, depending on the imaging mode (for example, whether a linear mode where a number of transducers transmit ultrasound waves in a same spatial direction, or a sector mode, where a number of transducers transmit ultrasound waves in different spatial directions), each column of transducer elements 104 may be coupled to a single transmit channel 108 and a single receive channel (110). In this example, the transmit channel 108 and receive channel 110 may receive composite signals, which composite signals combine signals received at each transducer element 104 within the respective column. In another example, i.e., during a different imaging mode, each transducer element 104 may be coupled to its dedicated transmit channel 108 and its dedicated receive channel 110. In some embodiments, a transducer element 104 may be coupled to both a transmit channel 108 and a receive channel 110. For example, a transducer element 104 may be adapted to create and transmit an ultrasound pulse and then detect the echo of that pulse in the form of converting the reflected ultrasonic energy into electrical energy.

The control circuitry 106 may be embodied as any circuit or circuits configured to perform the functions described herein. For example, the control circuitry 106 may be embodied as or otherwise include an application specific integrated circuit (ASIC), a field programmable gate array (FPGA), a system-on-a-chip, a processor and memory, a voltage source, a current source, one or more amplifiers, one or more digital-to-analog converters, one or more analog-to-digital converters, etc.

The illustrative computing device 112 may be embodied as any suitable computing device including any suitable components, such as one or more processors (i.e. one or more processing circuitries), one or more memory circuitries, one or more communication circuitries, one or more batteries, one or more displays, etc. As an example, the computing device 112 may include a processor that is configured to execute or interpret software, scripts, programs, functions, executables, or other instructions stored in a memory of the computing device, e.g., instructions of an application or applications that implement aspects of the present disclosure. The memory of the computing device may include computer-readable media, including a volatile memory device, a non-volatile memory device, or a combination thereof. The memory can include one or more read-only memory devices, random-access memory devices, buffer memory devices, or a combination of these and other types of memory devices.

In one embodiment, the computing device 112 may be integrated with the control circuitry 106, transducers 102, etc., into a single microelectronic package or single chip, or a single system on a chip (SoC), or a single ultrasound imaging device housing as suggested for example in the embodiment of FIG. 1. In other embodiments, some or all of the computing devices may be in a separate microelectronic package from the control circuitry, or in a separate device distinct from the ultrasound imaging device such as an ultrasound imaging probe, as suggested for example in the embodiment of in FIG. 2 as will be described in further detail below.

Each transducer element may have any suitable shape such as, square, rectangle, ellipse, or circle. The transducer elements may be arranged in a two-dimensional array arranged in orthogonal directions, such as in N columns and M rows as noted herein or may be arranged in an asymmetric (or staggered) rectilinear array.

Transducer elements 104 may have associated transmit driver circuits of associated transmit channels, and low noise amplifiers of associated receive channels. Thus, a transmit channel may include transmit drivers, and a receive channel may include one or more low noise amplifiers. For example, although not explicitly shown, the transmit and receive channels may each include multiplexing and address control circuitry to enable specific transducer elements and sets of transducer elements to be activated, deactivated or put in low power mode. It is understood that transducers may be arranged in patterns other than orthogonal rows and columns, such as in a circular fashion, or in other patterns based on the ranges of ultrasonic waveforms to be generated therefrom.

Figure 2:
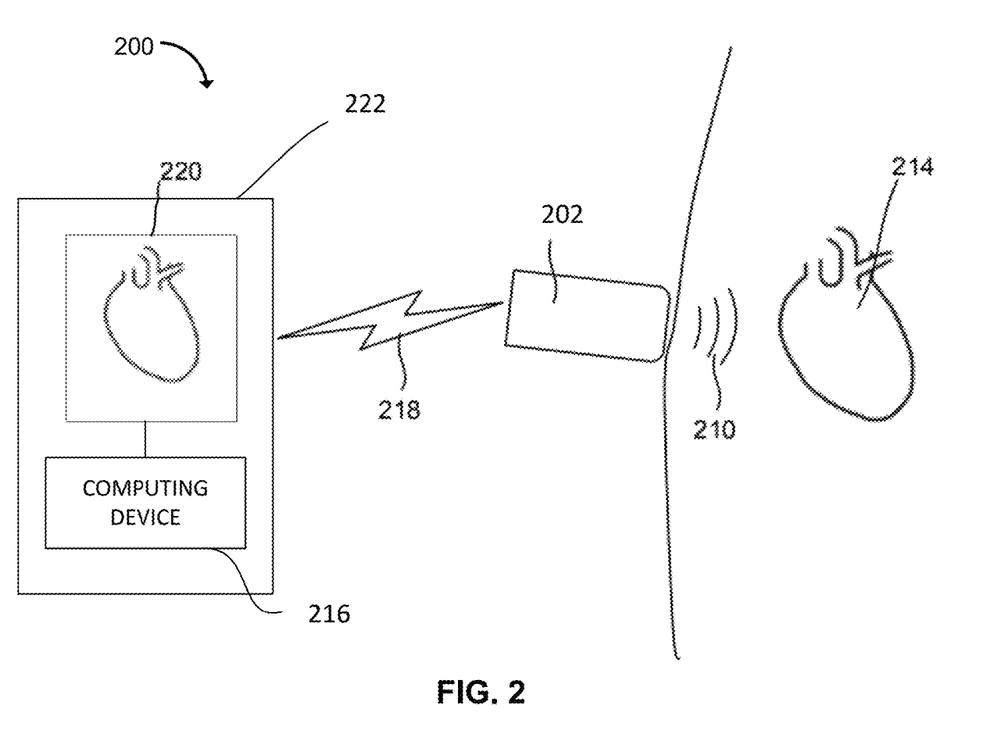
FIG. 2 is a diagram of an example imaging system in accordance with disclosed embodiments.

FIG. 2 illustrates an example imaging environment including an imaging system 200 according to an embodiment. The imaging system of FIG. 2 may include an ultrasound imaging device 202 (which may be similar to ultrasound imaging device 300 described below in the context of FIG. 3) and a computing system 222 which includes a computing device 216 and a display 220 coupled to the computing device 216, as will be described in further detail below.

As depicted in FIG. 2, the computing device 216 may, according to one embodiment, and unlike the embodiment of FIG. 1, be physically separate from the ultrasound imaging device 220. For example, the computing device 216 and display device 220 may be disposed within a separate device (in this context, the shown computing system 222, physically separate from imaging device 202 during operation) as compared with the components of the ultrasound imaging device 202. The computing system 222 may include a mobile device, such as cell phone or tablet, or a stationary computing device, which can display images to a user. In another example, as shown in FIG. 1 for example, the display device, the computing device, and associated display, may be part of the ultrasound imaging device 202 (now shown). That is, the ultrasound imaging device 100, computing device 216, and display device 220 may be disposed within a single housing.

A "computing device" as referred to herein may, in some embodiments, be configured to generate signals to at least one of cause an image of the object to be displayed on a display, or cause information regarding the image to be communicated to a user. Further, a "computing device," as referred to herein may, in some embodiments, be configured to receive sensor signals from sensor circuitry of an ultrasound imaging device, and to process those sensor signals to cause generation of execution signals to cause execution of ultrasound exam functions based on the sensor signals.

As depicted, the imaging system includes the ultrasound imaging device 202 that is configured to generate and transmit, via the transmit channels (FIG. 1, 108), pressure waves 210 toward an object, such as a heart 214, in a transmit mode/process. The internal organ, or other object to be imaged, may reflect a portion of the pressure waves 210 toward the ultrasound imaging device 202 which may receive, via a transducer (such as transducer 102 of FIG. 1), receive channels (FIG. 1, 110), control circuitry (FIG. 1, 106), the reflected pressure waves. The transducer may generate an electrical signal based on the received ultrasonic energy in a receive mode/process. A transmit mode or receive mode may be applicable in the context of imaging devices that may be configured to either transmit or receive, but at different times. However, as noted previously, some imaging devices according to embodiments may be adapted to be in both a transmit mode and a receive mode simultaneously. The system also includes a computing device 216 that is to communicate with the ultrasound imaging device 100 through a communication channel, such as a wireless communication channel 218 as shown, although embodiments also encompass within their scope wired communication between a computing system and imaging device. The ultrasound imaging device 100 may communicate signals to the computing device 216 which may have one or more processors to process the received signals to complete formation of an image of the object. A display device 220 of the computing system 222 may then display images of the object using the signals from the computing device.

An imaging device according to some embodiments may include a portable device, and/or a handheld device that is adapted to communicate signals through a communication channel, either wirelessly (using a wireless communication protocol, such as an IEEE 802.11 or Wi-Fi protocol, a Bluetooth protocol, including Bluetooth Low Energy, a mmWave communication protocol, or any other wireless communication protocol as would be within the knowledge of a skilled person) or via a wired connection such as a cable (such as USB2, USB 3, USB 3.1, and USB-C) or such as interconnects on a microelectronic device, with the computing device. In the case of a tethered or wired, connection, the ultrasound imaging device may include a port for receiving a cable connection of a cable that is to communicate with the computing device. In the case of a wireless connection, the ultrasound imaging device 100 may include a wireless transceiver to communicate with the computing device 216.

It should be appreciated that, in various embodiments, different aspects of the disclosure may be performed in different components. For example, in one embodiment, the ultrasound imaging device may include circuitry (such as the channels) to cause ultrasound waveforms to be sent and received through its transducers, while the computing device may be adapted to control such circuitry to the generate ultrasound waveforms at the transducer elements of the ultrasound imaging device using voltage signals, and further a processing of the received ultrasonic energy.

Figure 3:
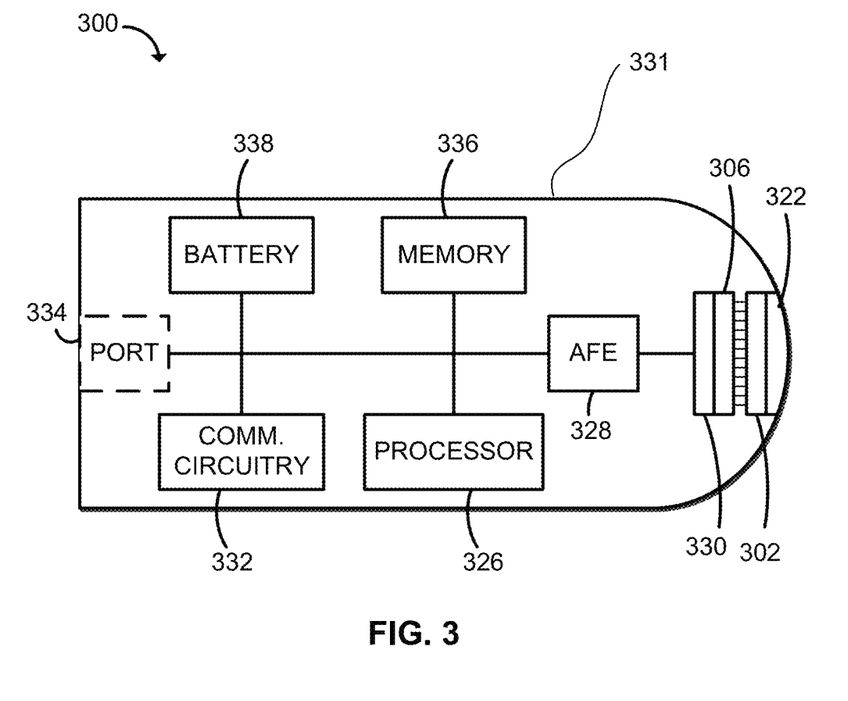
FIG. 3 illustrates an example imaging device in accordance with some disclosed embodiments.

FIG. 3 illustrates an example imaging device 300 according to some embodiments. The imaging device 300 may be similar to imaging device 100 of FIG. 1, or to imaging device 202 of FIG. 2, by way of example only. As described above, the imaging device may include an ultrasonic medical probe. FIG. 3 depicts transducer(s) 302 of the imaging device 300. As described above, the transducer(s) 302 may include arrays of transducer elements (e.g., 104 of FIG. 1) that are adapted to transmit and receive pressure waves (e.g., 210 of FIG. 2). In some examples, the imaging device 300 may include a coating layer 322 that serves as an impedance matching interface between the transducers 302 and the human body, or other mass or tissue through which the pressure waves (e.g., 210 of FIG. 2) are transmitted. In some cases, the coating layer 322 may serve as a lens when designed with the curvature consistent with focal length desired.

The imaging device 300 may be embodied in any suitable form factor. In some embodiments, part of the imaging device 300 that includes the transducers 302 may extend outward from the rest of the imaging device 100. The imaging device 300 may be embodied as any suitable ultrasonic medical probe, such as a convex array probe, a micro-convex array probe, a linear array probe, an endovaginal probe, endorectal probe, a surgical probe, an intraoperative probe, etc. In some embodiments, the user may apply gel on the skin of a living body before a direct contact with the coating layer 322 so that the impedance matching at the interface between the coating layer 322 and the human body may be improved. Impedance matching may reduce the loss of the pressure waves at the interface and the loss of the reflected wave travelling toward the imaging device 300 at the interface. In some examples, the coating layer 322 may be a flat layer to maximize transmission of acoustic signals from the transducer(s) 102 to the body and vice versa. The thickness of the coating layer 322 may be a quarter wavelength of the pressure wave (e.g., 210 of FIG. 2) to be generated at the transducer(s) 102.

The imaging device 300 also includes a control circuitry 306, such as one or more processors (e.g., in the form of an application-specific integrated circuit (ASIC chip or ASIC)) for controlling the transducers 302 (which may be implemented in the same or similar manner as transducers 102 of FIG. 1). The control circuitry 306 may be implemented in the same or similar manner as the control circuitry 106 of FIG. 1, and may be electrically connected to the transducers 302, e.g., by way of bumps or other similar types of electrical connectors. As described herein, the electrical connections to the transducers may be tested prior to their incorporation in the device 300 to ensure that the resulting imaging device 300 functions properly. The transducers 302 may be tested according to one or more of the methods described herein.

The imaging device 300 may also include one or more processors 326 for controlling the components of the imaging device 300. One or more processors 326 may be configured to, in addition to control circuitry 306, at least one of control an activation of transducer elements, process electrical signals based on reflected ultrasonic waveforms from the transducer elements or generate signals to cause a restoration of an image of an object being imaged by one or more processors of a computing device, such as computing device 112 of FIG. 1 or 216 of FIG. 2. One or more processors 326 may further be adapted to perform other processing functions associated with the imaging device. The one or more processors 326 may be embodied as any type of processors 326. For example, the one or more processors 326 may be embodied as a single or multi-core processor(s), a single or multi-socket processor, a digital signal processor, a graphics processor, a neural network compute engine, an image processor, a microcontroller, a field programmable gate array (FPGA), or other processor or processing/controlling circuit. The imaging device 100 may also include circuit(s) 328, such as Analog Front End (AFE), for processing/conditioning signals, and an acoustic absorber layer 330 for absorbing waves that are generated by the transducers 102 and propagated towards the circuits 328. That is, the transducer(s) 102 may be mounted on a substrate and may be attached to an acoustic absorber layer 330. This layer absorbs any ultrasonic signals that are emitted in the reverse direction (i.e., in a direction away from coating layer 322 in a direction toward port 334), which may otherwise be reflected and interfere with the quality of the image. While FIG. 3 depicts the acoustic absorber layer 330, this component may be omitted in cases where other components prevent a material transmission of ultrasound in the reverse direction. The analog front end 328 may be embodied as any circuit or circuits configured to interface with the control circuitry 306 and other components of the imaging device, such as the processor 326. For example, the analog front end 328 may include, e.g., one or more digital-to-analog converters, one or more analog-to-digital converters, one or more amplifiers, etc.

The imaging device may include a communication unit 332 for communicating data, including control signals, with an external device, such as the computing device (FIG. 2, 216), through for example a port 334 or a wireless transceiver. The imaging device 100 may include memory 336 for storing data. The memory 336 may be embodied as any type of volatile or non-volatile memory or data storage capable of performing the functions described herein. In operation, the memory 336 may store various data and software used during operation of the imaging device 100 such as operating systems, applications, programs, libraries, and drivers.

In some examples, the imaging device 100 may include a battery 338 for providing electrical power to the components of the imaging device 100. The selectable alteration of the channels may have a particularly relevant impact when the imaging device 100 includes a battery 338. For example, as the receive channels (e.g., 110 of FIG. 1) and transmit channels (e.g., 108 of FIG. 1) include components that draw power, the battery depletes over time. The consumption of power by these components in some examples may be rather large such that the battery 338 would drain in a short amount of time. This is particularly relevant when obtaining high quality images which consume significant amounts of power. The battery 338 may also include battery charging circuits which may be wireless or wired charging circuits (not shown). The imaging device may include a gauge that indicates a battery charge consumed and is used to configure the imaging device to optimize power management for improved battery life. Additionally or alternatively, in some embodiments, the imaging device may be powered by an external power source, such as by plugging the imaging device into a wall outlet.

It should be appreciated that, in some embodiments, various components of the imaging device 300 as shown in FIG. 3 may be omitted from an imaging device of embodiments herein, or may be included in other components separate from the imaging device 300. For example, in one embodiment, the one or more processors 326 may include some or all of the control circuitry 306. Additionally or alternatively, some or all of the components may be integrated into or form part of a system-on-a-chip (SoC) or multichip package.

Figure 4:
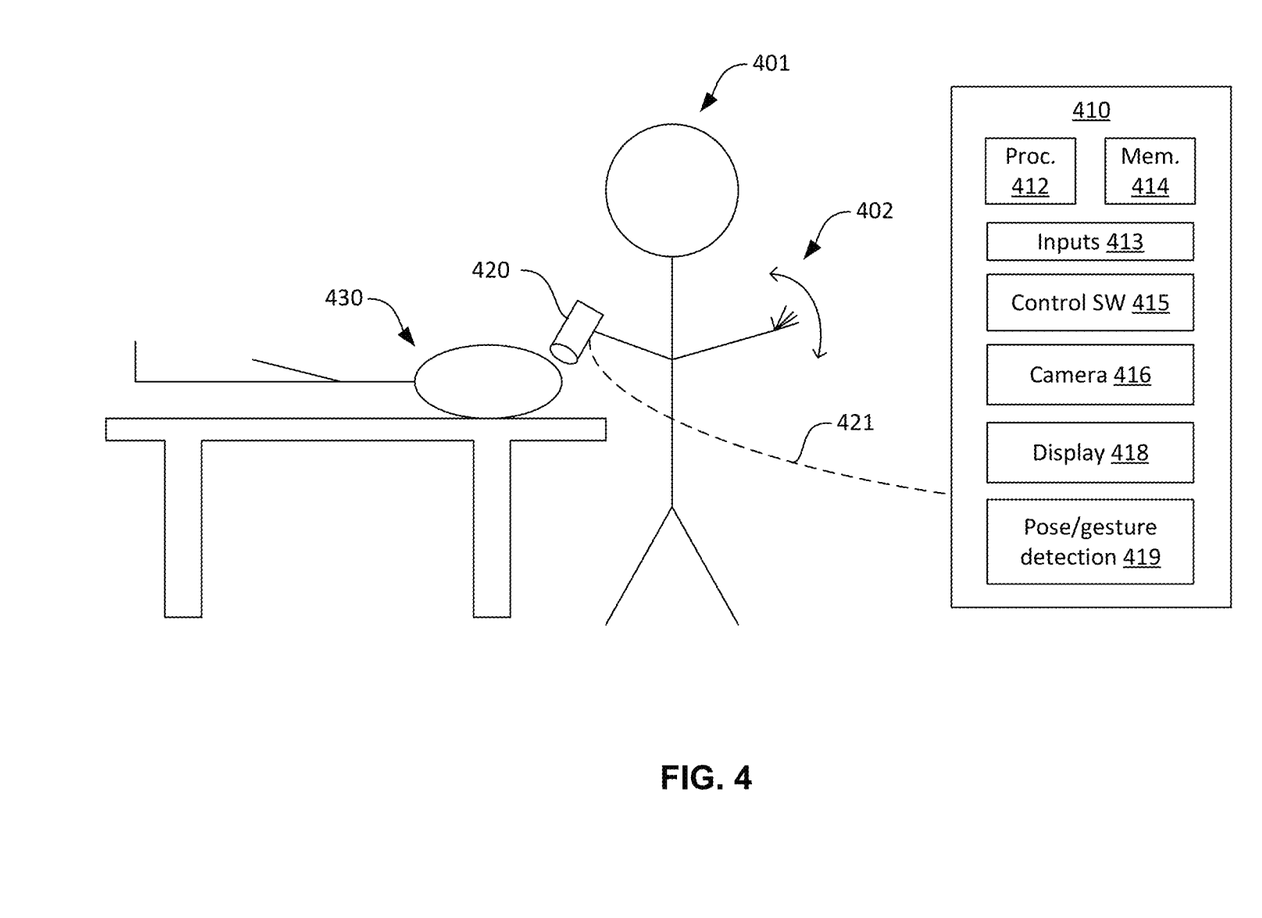
FIG. 4 illustrates an example ultrasound imaging system for detecting poses or gestures of a user to control the system in accordance with disclosed embodiments.

FIG. 4 illustrates an example ultrasound imaging system 410 for detecting poses or gestures 402 of a user 401 to control the system 410 in accordance with disclosed embodiments. In the example shown, a user 401 is performing an imaging procedure on a patient 430 using an ultrasound imaging device 420 coupled to the system 410 through a link 421, which may be a wired connection or a wireless link (e.g., a Bluetooth®-based or IEEE 802.11-based link). The ultrasound imaging device 420 may be implemented in the same or similar manner as one or more of the device 300 of FIG. 3, the imaging device 202 of FIG. 2, or the imaging device 100 of FIG. 1. The system 410 includes control software 415 that controls the operation of the different aspects of the system 410 to provide ultrasound imaging functionality. The control software 415 may, for example, detect inputs from the user 401 and perform various functions within the system 410 based on those inputs. The inputs may be detected at inputs 413, e.g., by a keyboard, buttons, trackball, etc., with which the user 401 may interact to control the system 410. The inputs may also be detected via detection of a pose or gesture 402 by the user 401 (via the camera 416), as described further below.

The system 410 also includes a camera 416 and a display 418. The display 418 may be implemented similar to the display 220 of FIG. 2, e.g., it may provide a display of images obtained from the ultrasound imaging device 420 from the patient 430 during the imaging procedure. The camera 416 may be implemented on the same side of the system 410 as the display 418, similar to a user-facing camera of a mobile computing device such as a tablet or phone (in some instances, for example, the system 410 may be implemented in a table computing device or a device with a similar form factor). That is, the camera 416 may be arranged within the system 410 in a way that allows it to obtain image and/or video of the user 401 during use. Although only one camera 416 is shown, the system 410 may include additional cameras to capture images and/or video of the user 401. Additional cameras may also be implemented external to the system 410 and coupled to the system 410, e.g., to capture images/video of the user 401 from a different angle.

The system 410 also includes pose/gesture detection software 419 to implement embodiments of the present disclosure. As described further below, the pose/gesture detection software 419 may receive data from the camera 416 (e.g., data for multiple images taken by the camera and/or video data obtained by the camera) and analyze the data to determine whether a pose and/or gesture performed by the user 401 has been detected. For example, the pose/gesture detection software 419 may implement or otherwise utilize a trained neural network (e.g., a deep neural network (DNN), a convolutional neural network (CNN), a deep-learning CNN (DCNN), or another type of neural network (NN)) to detect whether a pose or gesture has been performed by the user based on images or video obtained by the camera 416.

The pose/gesture detection software 419, for example, may detect whether the user 401 has performed a particular pose or gesture 402 with his/her hand. The pose or gesture 402 may be performed by the user 401 to provide a control command to the system 410. For example, the user 401 may perform the pose or gesture 402 to cause the system 410 to take a snapshot of an image, cause an image currently being displayed to be printed (e.g., by a printer of the system 410 or connected to the system 410), select something indicated on the display 418 (e.g., a button displayed on the screen for selection), zoom in or out on the image being displayed on the display 418, scroll up or down on the display 418, change screens or menus displayed on the display 418, or any other suitable command for the system 410. The system 410 may be implemented, in certain embodiments, to detect the pose or gesture with the pose/gesture detection software 419 and then pass an indication of the detected pose or gesture 402 to the control software 415, which can then interpret the pose or gesture as a particular command. That is, the pose/gesture detection software 419 may simply perform a detection role. However, in other embodiments, the pose/gesture detection software 419 may also perform the interpretive role as well, i.e., it can detect the pose/gesture 402 and pass a corresponding command to the control software 415.

Example poses or gestures may include a finger wiggle, a pinching motion where an index finger and thumb come together, reverse pinching motion where an index finger and thumb move apart after touching, an open palm, holding up 1, 2, 3, or 4 fingers, opening or closing the hand, or any other suitable pose or gesture that can be trained. The pose/gesture detection software 419 can detect poses and/or gestures based on, for example, identifying the different fingers or other features of a user's hand and tracking a distance or angle between the different fingers or other portions of the hand.

The system 410 further includes a processor 412 and memory 414. The processor 412 executes instructions, for example, the instructions of the visualization generation application 930. The processor 412 may be or include a general-purpose microprocessor, as a specialized co-processor or another type of data processing apparatus. In some cases, the processor 412 may be configured to execute or interpret software, scripts, programs, functions, executables, or other instructions stored in the computing system 920. In some instances, the processor 412 includes multiple processors or data processing apparatuses. The memory 414 includes one or more computer-readable media; for example, the memory 414 may include a volatile memory device, a non-volatile memory device, or a combination thereof. The memory 414 can include one or more read-only memory devices, random-access memory devices, buffer memory devices, or a combination of these and other types of memory devices. The memory 414 may store instructions (e.g., programs, codes, scripts, or other types of executable instructions) that are executable by the processor 412 (e.g., application code for controlling the ultrasound imaging system 410 (e.g., 415) and/or implementing the pose/gesture detection (e.g., 419) as described herein).

Figure 5:
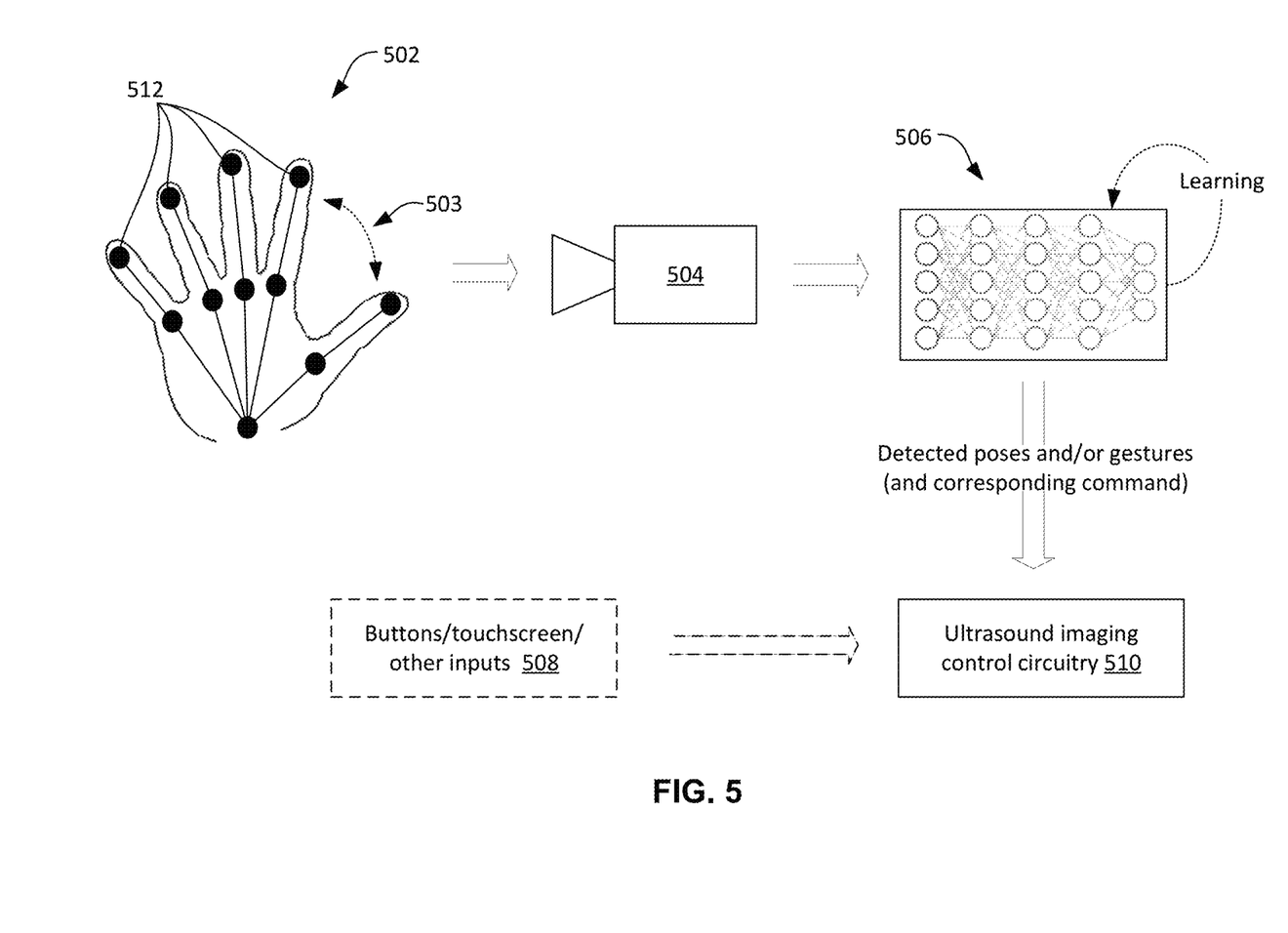
FIG. 5 illustrates an example process of modeling a hand for pose/gesture detection to control an ultrasound imaging system in accordance with disclosed embodiments.

FIG. 5 illustrates an example process of modeling a hand 502 for pose/gesture detection to control an ultrasound imaging system (e.g., 410) in accordance with disclosed embodiments. Generally, pose detection can be performed using a machine learning (ML) model (e.g., one that includes or uses a neural network (NN) such as 506, which may implemented, for example, as a DNN, CNN, DCNN, or another suitable type of NN) to estimate the pose of a person, or portion of the person, from an image or video based on determining spatial locations of particular body points (e.g., joints), which may be referred to as "keypoints". For instance, in particular embodiments, the ML model 506 can detect a human hand 502 in images/video data from a camera 504 and can detect certain keypoints 512 of the hand 502 as shown in FIG. 5. The model 506 may, in certain embodiments, be implemented in software of an ultrasound imaging system, such as in the pose/gesture detection software 419 of the ultrasound imaging system 410 of FIG. 4.

The model 506 can be trained, via one or more ML learning techniques, to detect particular poses of the hand or gestures of the hand. A pose, as used herein, may refer to a particular static position of the keypoints 512 with respect to each other, while a gesture, as used herein, may refer to a particular movement of a set (e.g., a subset) of the keypoints 512 with respect to each other. As an example, a pose may be the one shown in FIG. 5 with all five fingers of the hand open, while a gesture may refer to the movement 503 of the forefinger and thumb with respect to each other. The model 506 may be trained to detect particular poses or gestures, and to notify the ultrasound imaging circuitry 510 of the detected pose/gesture. For instance, the model 506 may be trained through an iterative process to detect particular poses. The ultrasound imaging circuitry 510 may then be programmed to associated particular commands of the ultrasound imaging system 410 with the poses/gestures. For example, the ultrasound imaging circuitry 510 may associate particular indications from the model 506 (e.g., indicating a reverse pinching motion) with particular commands of the system (e.g., to zoom in on an image of the display). However, in some embodiments, the model 506 may be trained to make the command associations and provide the command associated with a pose/gesture directly to the control circuitry 510.

The model 506 can then, in operation, monitor the position and/or changes in position of the keypoints 512 (e.g., distances between the keypoints or angles between the lines between the keypoints) to detect whether a particular pose or gesture has been performed by a user (e.g., 401) in front of the camera. For instance, the model 506 may detect the movement 503 between keypoints 512 of the thumb and forefinger (and/or other fingers). In certain embodiments, when a particular pose or gesture is detected by the model 506, an indication of the detected pose/gesture may be provided to ultrasound imaging control circuitry 510, which can then use the indication to determine whether the detected pose or gesture is associated with a particular command of the system. In other embodiments, the model 506 may provide the associated command instead, as described above. The circuitry 510 can then implement the command associated with the detected pose/gesture in a similar manner as if the command were entered to the system via a traditional input, e.g., buttons, touchscreen, or other type of input device 508. Thus, the pose/gesture detection provided by the model 506 may allow for control of the ultrasound imaging system in lieu of traditional inputs, such as via inputs 508; however, it may also provide for control of the system in parallel with commands or inputs provided via the traditional inputs. This can allow for the provision of inputs to the system without the need for physical touch, which can be beneficial in medical or other types of fields where there are sanitary concerns. In addition, it can provide parallel input paths to the system as well.

Figure 6A:
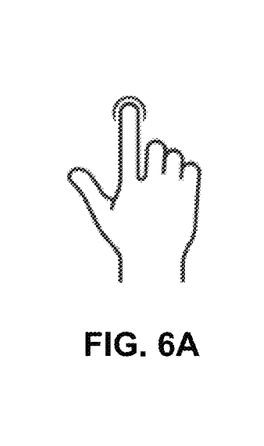
FIGS. 6A-6C illustrate example poses that may be trained and/or detected in accordance with disclosed embodiments.
Figure 6B:
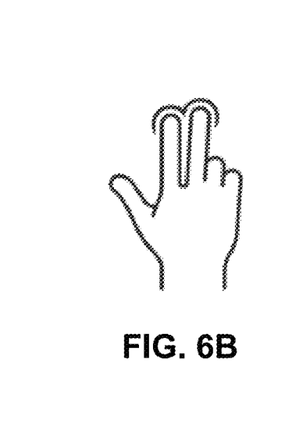
Figure 6C:
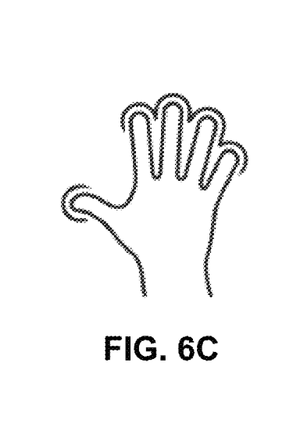
Figure 7A:
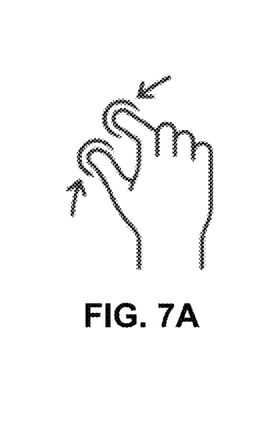
FIGS. 7A-7C illustrate example gestures that may be trained and/or detected in accordance with disclosed embodiments.
Figure 7B:
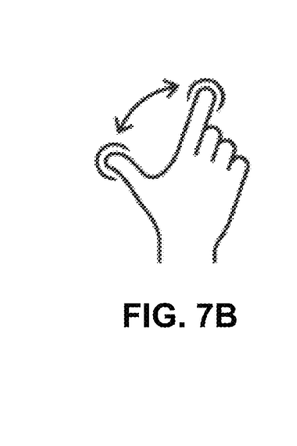
Figure 7C:
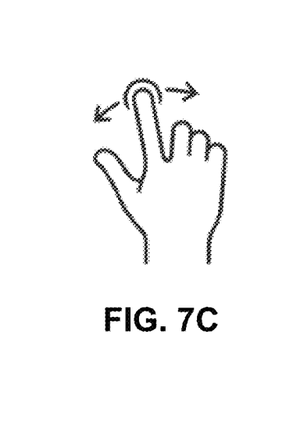

FIGS. 6A-6C illustrate example poses that may be trained and/or detected, while FIGS. 7A-7C illustrate example gestures that may be trained and/or detected in accordance with disclosed embodiments. In particular, FIG. 6A illustrates a pose with a thumb and one finger extended, FIG. 6B illustrates a pose with a thumb and two fingers extended, and FIG. 6C illustrates a pose with all fingers extended/an open hand. FIG. 7A illustrates an example pinching motion, FIG. 7B illustrates an example reverse pinching motion, and FIG. 7C illustrates a wagging or wiggled index finger gesture. Each of these poses and gestures can be associated with a different particular command for an ultrasound imaging system, as described above. Moreover, there may be a number of additional (or fewer) poses and gestures that can be associated with particular commands of an ultrasound imaging system. In some embodiments, multiple poses or gestures can be associated with the same command (e.g., N poses/gestures to one command). Further, in some embodiments, a pose and a gesture can be detected in combination and associated with a particular command. For instance, the pose shown in FIG. 6A can be used to first select an object on a display and the finger can then be moved to control a placement of the object on the display.

Figure 8:
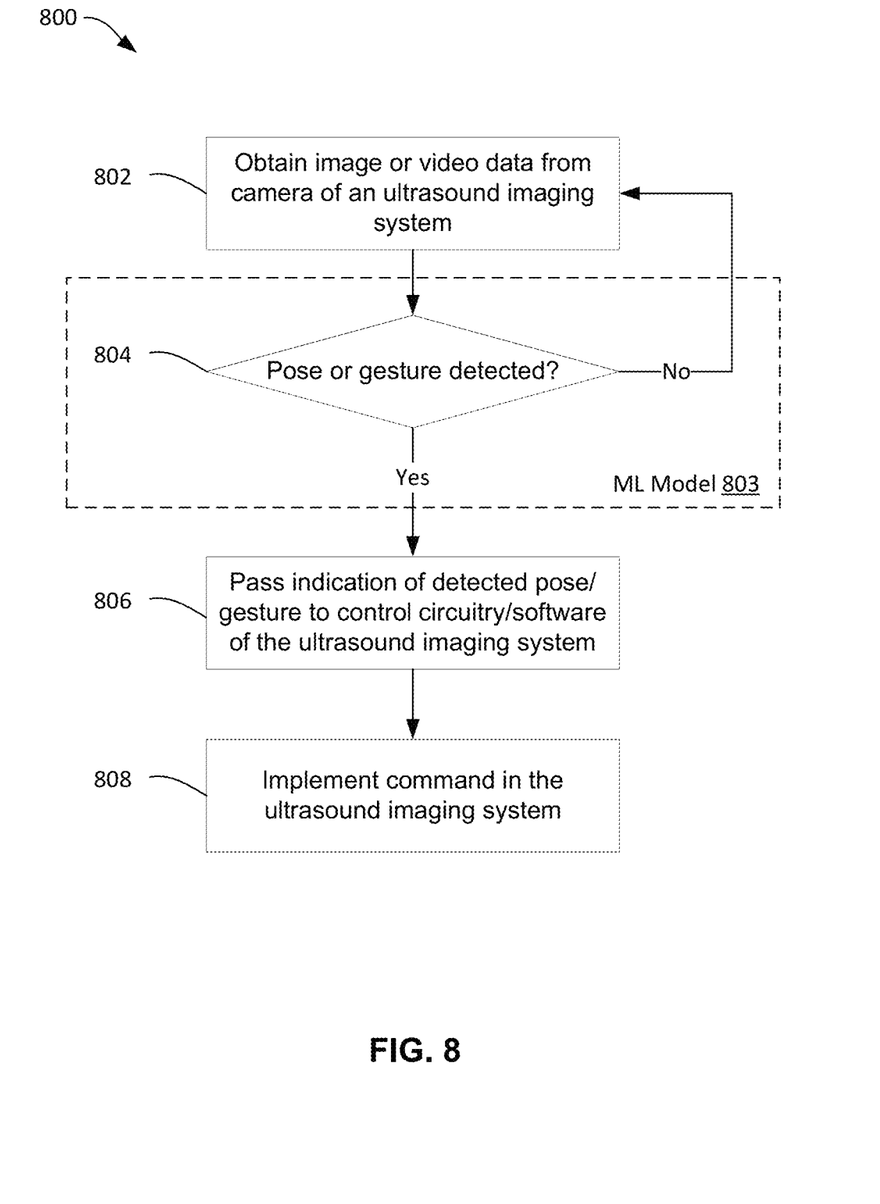
FIG. 8 is a flow diagram of an example process of controlling an ultrasound imaging system using detected poses or gestures according to disclosed embodiments.

FIG. 8 is a flow diagram of an example process 800 of controlling an ultrasound imaging system using detected poses or gestures according to disclosed embodiments. The example process 800 can be performed by one or more components of an apparatus (such as any part of, including one or more processors of) a computing device or computing system (e.g., the system 410 of FIG. 4) according to some embodiments. In some embodiments, one or more aspects of the example process 800 are embodied as instructions in a computer-readable medium that, when executed by a machine (e.g., a processor of a computing device) cause the machine to implement the operations described below. Although certain operations are shown, there may be additional (or fewer) operations in certain embodiments.

At operation 802, image or video data is obtained from a camera of an ultrasound imaging system, e.g., camera 416 of the system 410 of FIG. 4. At operation 804, it is determined whether a pose or gesture is detected in the image or video data obtained by the camera. The pose or gesture may be detected using an ML model 803 as shown, which may include, use, or otherwise implement a neural network (e.g., a DNN, CNN, DCNN, or another type of NN). At 806, an indication of the detected command is provided by the ML model 803 to control circuitry or software of the ultrasound imaging system. Finally, at operation 808, a command corresponding to the detected pose or gesture is implemented in the ultrasound imaging system. The command may be any of the examples described herein, or any other suitable type of command that can be implemented in or executed by an ultrasound imaging system based on an input. The command may be determined by determining whether there exists an association in the ultrasound imaging system of the detected pose or gesture with a particular command. In some instances, there may not be any command association, in which no command may be impelemented.

Figure 9:
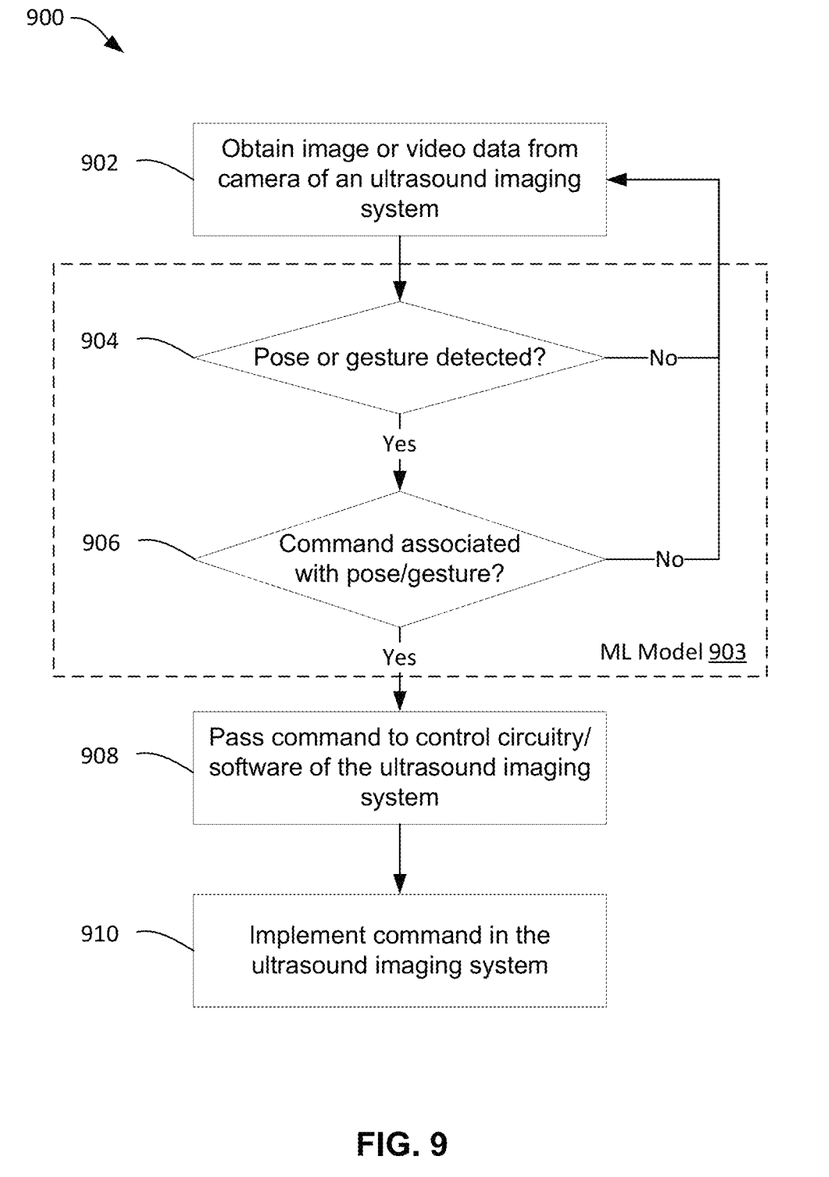
FIG. 9 is a flow diagram of another example process of controlling an ultrasound imaging system using detected poses or gestures according to disclosed embodiments.

FIG. 9 is a flow diagram of an example process 900 of controlling an ultrasound imaging system using detected poses or gestures according to disclosed embodiments. The example process 900 can be performed by one or more components of an apparatus (such as any part of, including one or more processors of) a computing device or computing system (e.g., the system 410 of FIG. 4) according to some embodiments. In some embodiments, one or more aspects of the example process 900 are embodied as instructions in a computer-readable medium that, when executed by a machine (e.g., a processor of a computing device) cause the machine to implement the operations described below. Although certain operations are shown, there may be additional (or fewer) operations in certain embodiments.

At operation 902, image or video data is obtained from a camera of an ultrasound imaging system, e.g., camera 416 of the system 410 of FIG. 4 At operation 904, it is determined whether a pose or gesture is detected in the image or video data obtained by the camera. The pose or gesture may be detected using an ML model 903 as shown, which may include, use, or otherwise implement a neural network (e.g., a DNN, CNN, DCNN, or another type of NN). At operation 906, the ML model 903 further determines whether there exists a command that is associated with the detected pose or gesture. At operation 908, the command corresponding to the detected pose or gesture is passed to the control circuitry or software of the ultrasound imaging system, and at operation 910, the command corresponding to the detected pose or gesture is implemented in the ultrasound imaging system. The command may be any of the examples described herein, or any other suitable type of command that can be implemented in or executed by an ultrasound imaging system based on an input.

Aspects of the present disclosure have been described with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

While preferred embodiments of the present disclosure have been shown and described herein, it will be obvious to those skilled in the art that such embodiments are provided by way of example only. It is not intended that embodiments be limited by the specific examples provided within the specification. While embodiments of the disclosure have been described with reference to the aforementioned specification, the descriptions and illustrations of the embodiments herein are not meant to be construed in a limiting sense. Numerous variations, changes, and substitutions will now occur to those skilled in the art without departing from the concepts of the present disclosure. Furthermore, it shall be understood that all aspects of the various embodiments are not limited to the specific depictions, configurations, or relative proportions set forth herein, which depend upon a variety of conditions and variables. It should be understood that various alternatives to the embodiments described herein may be employed. It is therefore contemplated that the disclosure also covers any such alternatives, modifications, variations or equivalents.

EXAMPLES

Illustrative examples of the technologies disclosed herein are provided below. An embodiment of the technologies may include any one or more, and any combination of, the examples described below.

Example 1 is a method comprising receiving image or video data from a camera of an ultrasound imaging system; detecting a pose or gesture in the image or video data using a machine learning (ML) model; and implementing a command for the ultrasound imaging system based on the detected pose or gesture.

Example 2 includes the subject matter of Example 1, wherein the ML model comprises a neural network.

Example 3 includes the subject matter of Example 2, wherein the neural network is one of a deep neural network, a convolutional neural network, or a deep-learning convolutional neural network.

Example 4 includes the subject matter of any one of Examples 1-3, further comprising determining that the command corresponds to the detected pose or gesture using the ML model.

Example 5 includes the subject matter of any one of Examples 1-3, wherein the pose or gesture is detected using a first software application and the command corresponding to the detected pose or gesture is determined using a second software application based on an indication provided by the first software application of the detected pose or gesture to the second software application.

Example 6 includes the subject matter of Example 5, wherein the second software application further controls operation of the ultrasound imaging system.

Example 7 includes the subject matter of any one of Examples 1-6, wherein the pose or gesture is detected based on positions of keypoints of a user detected in the image or video data.

Example 8 includes the subject matter of Example 7, wherein a pose is detected based on static positions of the keypoints of the user with respect to one another.

Example 9 includes the subject matter of Example 7, wherein a gesture is detected based on changes in positions of the keypoints of the user with respect to one another.

Example 10 includes the subject matter of any one of Examples 1-9, wherein the pose or gesture is detected in a hand of a user.

Example 11 includes the subject matter of any one of Examples 1-10, wherein the command is to perform at least one of: taking snapshot of an image displayed by the ultrasound imaging system, causing an image displayed by the ultrasound imaging system to be printed, making a selection in a menu displayed by the ultrasound imaging system, zooming in or out of an image displayed by the ultrasound imaging system, scrolling a menu or image displayed by ultrasound imaging system, and changing a screen or menu displayed by the ultrasound imaging system.

Example 12 includes one or more computer-readable media comprising instructions that, when executed by one or more processors, cause the one or more processors to: access image or video data from a camera; detect a pose or gesture based on the image or video data using a machine learning (ML) model; and cause a command to be implemented in the ultrasound imaging system based on the detected a pose or gesture.

Example 13 includes the subject matter of Example 12, wherein the instructions are further to cause the one or more processors to determine that the command corresponds to the detected pose or gesture using the ML model.

Example 14 includes the subject matter of Example 12 or 13, wherein the instructions are further to cause the one or more processors to cause an indication of the detected pose or gesture to be provided to a control circuitry of the ultrasound imaging system.

Example 15 includes the subject matter of any one of Examples 12-14, wherein the instructions are further to cause the one or more processors to detect keypoints of a user in the image or video data and detect the pose or gesture based on positions of the keypoints with respect to one another.

Example 16 includes the subject matter of any one of Examples 12-15, wherein the pose or gesture is detected based on a hand of a user detected in the image or video data from the camera.

Example 17 includes the subject matter of any one of Examples 12-16, wherein the ML model is a neural network.

Example 18 is an ultrasound imaging system comprising: a camera; a memory storing instructions; and processor circuitry to execute the instructions to: access image or video data from the camera; detect a pose or gesture in the image or video data using a machine learning (ML) model; and implement a command for the ultrasound imaging system based on the detected pose or gesture.

Example 19 includes the subject matter of Example 18, wherein the processor circuitry is to execute the instructions to detect keypoints of a user in the image or video data and detect the pose or gesture based on positions of the keypoints with respect to one another.

Example 20 includes the subject matter of Example 18 or 19, wherein the pose or gesture is detected based on a hand of a user detected in the image or video data from the camera.

Example 21 is one or more computer-readable media comprising instructions that, when executed by a processor, perform the operations of any one of Examples 1-11.

Example 22 is a system comprising: a memory storing instructions; and processor circuitry to execute a set of instructions to implement the method of any one of Examples 1-11.

Example 23 includes an apparatus comprising means for performing the method of any one of Examples 1-11.

Example 24 includes one or more computer-readable media comprising a plurality of instructions stored thereon that, when executed, cause one or more processors to perform the method of any one of Examples 1-11.

Example 25 is a product comprising one or more tangible computer-readable non-transitory storage media comprising computer-executable instructions operable to, when executed by at least one computer processor, enable the at least one processor to perform the method of any one of Examples 1-11.

What is claimed is:

1. A method comprising:
   receiving image or video data from a camera of an ultrasound imaging system;
   detecting a pose or gesture in the image or video data using a machine learning (ML) model, wherein the pose or gesture is detected independent of proximity to control inputs of the ultrasound imaging system; and
   implementing a command for the ultrasound imaging system based on the detected pose or gesture.

2. The method of claim 1, wherein the ML model comprises a neural network.

3. The method of claim 2, wherein the neural network is one of a deep neural network, a convolutional neural network, or a deep-learning convolutional neural network.

4. The method of claim 1, further comprising determining that the command corresponds to the detected pose or gesture using the ML model.

5. The method of claim 1, wherein the pose or gesture is detected using a first software application and the command corresponding to the detected pose or gesture is determined using a second software application based on an indication provided by the first software application of the detected pose or gesture to the second software application.

6. The method of claim 5, wherein the second software application further controls operation of the ultrasound imaging system.

7. The method of claim 1, wherein the pose or gesture is detected based on positions of keypoints of a user detected in the image or video data.

8. The method of claim 7, wherein a pose is detected based on static positions of the keypoints of the user with respect to one another.

9. The method of claim 7, wherein a gesture is detected based on changes in positions of the keypoints of the user with respect to one another.

10. The method of claim 1, wherein the pose or gesture is detected in a hand of a user.

11. The method of claim 1, wherein the command is to perform at least one of: taking snapshot of an image displayed by the ultrasound imaging system, causing an image displayed by the ultrasound imaging system to be printed, making a selection in a menu displayed by the ultrasound imaging system, zooming in or out of an image displayed by the ultrasound imaging system, scrolling a menu or image displayed by ultrasound imaging system, and changing a screen or menu displayed by the ultrasound imaging system.

12. One or more computer-readable media comprising instructions that, when executed by one or more processors, cause the one or more processors to:
   access image or video data from a camera;
   detect a pose or gesture based on the image or video data using a machine learning (ML) model, wherein the detected pose or gesture is independent of proximity to control inputs of the ultrasound imaging system; and
   cause a command to be implemented in the ultrasound imaging system based on the detected a pose or gesture.

13. The computer-readable media of claim 12, wherein the instructions are further to cause the one or more processors to determine that the command corresponds to the detected pose or gesture using the ML model.

14. The computer-readable media of claim 12, wherein the instructions are further to cause the one or more processors to cause an indication of the detected pose or gesture to be provided to a control circuitry of the ultrasound imaging system.

15. The computer-readable media of claim 12, wherein the instructions are further to cause the one or more processors to detect keypoints of a user in the image or video data and detect the pose or gesture based on positions of the keypoints with respect to one another.

16. The computer-readable media of claim 12, wherein the pose or gesture is detected based on a hand of a user detected in the image or video data from the camera.

17. The computer-readable media of claim 12, wherein the ML model is a neural network.

18. An ultrasound imaging system comprising:
   a camera;
   a memory storing instructions; and
   processor circuitry to execute the instructions to:
      access image or video data from the camera;
      detect a pose or gesture in the image or video data using a machine learning (ML) model, wherein the pose or gesture is independent of proximity to control inputs of the ultrasound imaging system; and
      implement a command for the ultrasound imaging system based on the detected pose or gesture.

19. The system of claim 18, wherein the processor circuitry is to execute the instructions to detect keypoints of a user in the image or video data and detect the pose or gesture based on positions of the keypoints with respect to one another.

20. The system of claim 18, wherein the pose or gesture is detected based on a hand of a user detected in the image or video data from the camera.

* * * * *